United States Patent [19]

Schuster et al.

[11] Patent Number: 5,584,814
[45] Date of Patent: Dec. 17, 1996

[54] SYRINGE ACTUATION SYSTEM

[76] Inventors: John H. Schuster, 708 Whipporwill Rd., Derby, Kans. 67037; John F. Schlyer, 11607 W. Cindy, Wichita, Kans. 67212

[21] Appl. No.: 378,509

[22] Filed: Jan. 26, 1995

[51] Int. Cl.[6] .................................................. A61M 5/00
[52] U.S. Cl. ........................ 604/187; 604/141; 222/326
[58] Field of Search .......................... 604/181, 185–187, 604/70, 72, 208, 214, 218, 246, 141; 222/173, 326, 334, 381; 141/27, 378

[56] References Cited

U.S. PATENT DOCUMENTS

| | | | |
|---|---|---|---|
| 3,935,883 | 2/1976 | Stach et al. | 141/27 |
| 4,155,490 | 5/1979 | Glenn | 222/327 |
| 4,187,890 | 2/1978 | Stach et al. | 141/27 |
| 4,212,298 | 7/1980 | Gezari | 604/121 |
| 4,426,024 | 1/1984 | Hogan | 222/173 |
| 4,944,726 | 7/1990 | Hilal et al. | 604/143 |

*Primary Examiner*—Randall L. Green
*Assistant Examiner*—Perry E. Van Over
*Attorney, Agent, or Firm*—Bradley P. Sylvester

[57] ABSTRACT

A portable and hand held syringe filling device, having a frame that forms a curved channel, and one or more bulkheads fixed to the frame, that grip the barrel and flanges of a hypodermic syringe. A double acting air cylinder is fixed to one of the bulkheads, and is positioned within the frame channel, with the moving rod portion fixed to a slider having a thumb plate gripper that grips the thumb plate and plunger of a hypodermic syringe. The amount of air pressure and flow rate of the air pressure is specifically tailored to actuate the double action air cylinder, to provide an exact draw and dispense force on the syringe plunger. An adjustable stop is used to allow the syringe filling device to act as a pump, that delivers metered portions of liquid to target containers.

13 Claims, 2 Drawing Sheets

SYRINGE ACTUATION SYSTEM

BACKGROUND OF THE INVENTION

Certain medical treatments often require the use of medications injected intravenously, or subcutaneously, into the patient. These medications often have standard dosage amounts, tailored to fit the individual needs of different patients. Hospitals have a particularly high use of syringe-administered medications, requiring a substantial number of syringes to be filled daily, to meet their demands.

Typically, hospitals employ their pharmacy technicians or nurses to fill syringes. Pharmaceutical medications are purchased in large source containers that are then transferred to syringes or target containers. To fill a syringe, a technician must position the syringe by either inserting the syringe needle into the source container, or attach the syringe nozzle to a sterile catheter tubing that can deliver the desired medication. Once the syringe is in position, the plunger is directed forwards or backwards, keeping the syringe unit still, to avoid effecting the integrity of the needle or source container. Smaller source bottle containers, i.e., vials, may require the injection of air into the container before the substance is withdrawn.

The typical manual syringe filling procedure places a significant level of stress on the arms, wrists and fingers of the technicians. The stress is exaggerated, due to the repetitious and forceful movements of the wrist and fingers, reduced blood flow to the hands due to static muscle flexing of the upper arms, and the forceful grasping of the syringe during the filling and dispensing process. This repetitive strain to the musculoskeletal system can lead to cumulative trauma disorders like tendinitis and carpal tunnel syndrome. To avoid such physical problems, the stress involved in the filling and dispensing of medications must be reduced.

The type of substance, and/or the size of the syringe being filled, can vary the difficulty of the filling process. Syringes that have a volume capacity of more than twenty cubic centimeters are difficult to fill, due to the amount of fluid that they contain. A continuous pull on the plunger creates the necessary partial vacuum, so that normal atmospheric pressure can force the liquid through the syringe needle or nozzle into the syringe cavity. The amount of physical effort, and length of sustained pull on the plunger, increases when the substance is a dense liquid solution exhibiting a high level of viscosity.

Syringe filling must be a precise process, to gain the proper benefits. Errors in filling syringes can result in problems for the target patient. If the amount of medication administered is not the proper dosage, the patient suffers, and the medical care provider can be held liable for the error. Since issues of human health and recuperation often depend on whether the patient receives the proper amount of medication, the need for equipment that reduces stress on the technician filling the syringes, and reduces the likelihood of error in the filling process, is of extreme importance.

Prior mechanisms have been introduced as precision measuring devices, which can measure out multiple dosage units, generally from a pumping syringe. Some have incorporated adjustable systems into them, which allow a user to vary the dosage amount dispensed. While there may be some usefulness for the prior apparatus in dispensing vaccines and other types of standard dosage medications, the operation and use of these apparatuses are cumbersome when the intended use is for individual syringes with varied dosage amounts rather than a uniform metered amount. The prior apparatuses have limited mobility, curtailing their ability to deal with a variety of source containers and with the dislodging of air bubbles within a syringe.

This invention is portable, and fits within the manual syringe filling process currently in use at hospitals around the country, and taught at leading medical institutions. Portability and ergonomic design reduce musculoskeletal stress on technicians, promoting enhanced productivity and higher accuracy.

U.S. Pat. No. 2,966,175 (D. F. Hyde) reveals a pump system with a liquid delivery apparatus. A motor pulls on the plunger of a large syringe, causing the syringe to fill with the desired liquid substance. Once the syringe is filled, it is ready for delivery of the liquid. The intended use of this apparatus was to meter out specific amounts of substances into other target containers. The syringe was not intended for removal from the apparatus, nor did it have the capability for various positions. It was simply a pumping mechanism, when filled with the liquid medication.

In U.S. Pat. No. 3,935,883, (Stach et al) a syringe was again used as the pumping unit, in which the plunger was urged toward the rear of the syringe, and a fluid substance was drawn into the syringe barrel. The same motor would then urge the plunger toward the front of the syringe, pumping or forcing the fluid substance out of the syringe. Valves in a supply and delivery tube directed the liquid substance into the syringe for filling, and into a target syringe upon the pumping cycle. This apparatus was limited to the use of dispensing a uniform dosage, as would be needed for vaccines. The unit was not portable, or hand held, and all medications had to be positioned in relationship to the pumping syringe.

U.S. Pat. No. 4,155,490 (Glenn) provided a syringe and a mechanized frame that urged a syringe plunger back and forth in the syringe. This apparatus was cumbersome, and had no realistic means of being held and operated unless on a stable surface. The syringe was secured to a frame, and used as part of a pumping or graduated dispensing system. The syringe was not intended to be filled and removed, so another syringe could take its place, since the syringe was held in place by a securing clamp.

U.S. Pat. No. 4,187,890 (Paul E. Stach et al) disclosed an apparatus for use in filling small containers, using a pumping syringe during the dispensing process. The pumping syringe was fixed to a bulky framework and had no mobility. If a target syringe was used, as the small container to be filled, the fluid substance was injected into the target syringe, using pressure applied from the pumping syringe.

None of the prior art allows for a hand held unit to operate both as a portable manual single syringe filler and/or dispenser, and a repetitive uniform dosage dispenser. A hand held unit offers convenience of use, and manipulation for obtaining or dispensing medication, which could not be accomplished with a stationary table unit.

The prior inventions lack the ergonomic features, use of air pressure for the drawing and dispensing force, and mobility necessary to fill individual syringes accurately and without stress on the operator. This invention features a frame, which is designed to be held with a neutral wrist posture, and manipulated by the operator during the manual syringe filling process. The use of air pressure to manipulate the syringe results in a smoother operation and less repetitive stress on the operator and mechanical parts during the process. Additionally, the use of pressurized air, or inert gas, does not provide a potential ignition source, as an electrically driven motor system would. Pressurized gas can be tailored to give a specific pushing and pulling force on the syringe plunger, to operate effectively with liquids of varying viscosities.

SUMMARY OF THE INVENTION

It is an object of this invention to provide a portable apparatus that can fill or dispense a desired amount of liquid from a syringe without placing repetitive physical stress on the operator.

It is a further object of this invention to provide an apparatus that may be used on a work table surface, or hand held and operated at any desired angle or position.

It is a further object of this invention to provide an apparatus that is portable and hand held, when functioning as a single syringe filler/dispenser, and also when used as a repetitive pumping unit.

It is a further object of this invention to provide an apparatus that may be used to fill a wide range of syringe sizes and types, with liquid substances that have a varied range of viscosity.

It is a further object of this invention to provide an apparatus that can vary the amount of force on the plunger during the filling or dispensing process, allowing the operator to tailor the pressure force and flow rates necessary to fill and dispense liquids having different viscosities.

It is a further object of this invention to provide an apparatus that may be used to fill a target syringe or container with a specific amount of liquid substance, either uniquely, or in a repetitive manner, and can be used to remove any undesired air bubbles from the interior cavity of the syringe, without having to resort to thumping the syringe with a finger.

The apparatus relates to a syringe filler, using air pressure to provide the necessary force to the syringe plunger, during both the filling and dispensing of various liquids. All working components are ergonomically designed and positioned, to minimize physical stress on the operator, so that they can fill/dispense syringes over long time periods. The syringe filler can be-used on a work table surface, or it can be hand held while in operation. It can interchangeably function as a single syringe filler/dispenser, or as a repeating unit dosage pump dispenser.

A syringe has a nozzle at its front end, a syringe barrel defining a cavity for containing liquids, and a plunger slidably disposed within the syringe barrel. The front end of the plunger has a plunger seal, which contacts the inner walls of the cavity, creating an airtight seal against the walls of the barrel cavity. A thumb plate is located on the rear end of the plunger, which is grasped or pulled, during filling of the syringe, or pushed into the barrel cavity to dispense or force liquid out of the syringe.

Flanges extend outward near the rear end of the syringe barrel. The general purpose for the flanges on a syringe, is to give the user a means to hold or grip the syringe barrel, when the plunger is being pushed or pulled. When the flange and the thumb plate are forced toward each other, the plunger slides deeper into the syringe cavity, dispensing the syringe contents out through the nozzle or needle.

The syringe filler has a front bulkhead, with supporting feet on the bottom side, and a top side defining a syringe barrel rest. The sides of the syringe barrel rest define a curved channel that follows a circular arc path. The channel sides extend around slightly more than 180 degrees of the circular arc path, so when a syringe barrel is pushed into the syringe barrel rest, it is gripped by the ends of the curved channel sides.

A double acting air cylinder (air cylinder) has a threaded front end, extending through a hole in the front bulkhead, and is secured using a nut tightened over the threaded portion to hold the double acting air cylinder firmly to the front bulkhead. The air cylinder has a front body, and a rear rod, which is slidably disposed within the front body and extends out the rear end of the body. The air cylinder is actuated, using air pressure delivered to two ports located on the body of the air cylinder.

A rear bulkhead is positioned and fixed near the rear end of the front air cylinder body. A spacer surrounds the air cylinder body, and separates the front bulkhead from the rear bulkhead. Both the front and rear bulkheads remain stationary, in relationship to each other, during any actuation of the double acting air cylinder.

The top of the rear bulkhead extends vertically out of the frame channel, with a curved channel similar to the front bulkhead channel. This channel has curved sides, that follow a circular path extending slightly over 180 degrees. The rear portion of a syringe barrel is pressed or snapped into position, in a manner similar to the front bulkhead. Any horizontal movement of the syringe barrel is prevented by a flange slot that holds the flanges on the syringe barrel. The flange slot is designed so that it can receive the flanges on the syringe barrel, and has sufficient depth, so that the movement of the flanges are not hindered when the syringe barrel is rotated. Preferably, the syringe barrel will be able to rotate 360 degrees, while the syringe barrel flanges are situated within the flange slot, so that the graduation marks on the syringe can be properly observed by the operator.

A frame, having an U-shaped channel, is fixed to the sides of the front bulkhead and rear bulkhead. The U-shaped channel extends the length of the syringe filling apparatus, with the air cylinder being situated within the frame channel. The frame is ergonomically designed, with a shape and size that allows the operator to easily grasp it, and maneuver it with either their right or left hand.

A sliding sleeve, or "slider," is attached to the end of the rear rod portion that extends from the body of the air cylinder. The slider is attached to the air cylinder rod by fixing the slider to an end cap, that has a hole which allows the threaded end of the air cylinder rod to protrude through. A nut or bumper is tightened on the rod's threaded portion, fixing the end cap and slider firmly to the rod. The slider covers the rod when it is extended from the body, and has an inner diameter that allows it to slide over the body of the air cylinder, as the rod is withdrawn into it.

A thumb plate gripper is fixed to the front end of the slider, and extends vertically out of the frame channel. The top part of the thumb plate gripper defines a groove, that can receive the thumb plate of a syringe. This groove has a depth that allows the syringe thumb plate to move freely when the syringe barrel is rotated.

To mount a syringe into the syringe filler, the syringe is snapped into the front and rear bulkhead channels, with the flanges fitting within the flange slot, and the thumb plate gripper fitting in the thumb plate gripper groove. When the syringe is in position, its length parallels the air cylinder and frame. The syringe barrel is unable to slide horizontally, due to the flanges being held in the flange slot, and does not move vertically, due to the gripping action of the front and rear bulkhead channels. The syringe barrel may be rotated, while fitted to the syringe filler, so that the operator can properly view the graduation markings. Removal of the syringe is accomplished by simply grasping the syringe barrel, and pulling it vertically, so that the barrel snaps out of the front and rear bulkhead's curved channel. The flanges and thumb plate simply slide out of their respective slot or groove.

The air cylinder can be actuated by any pressurized gas, such as dry compressed air, gaseous nitrogen, or other inert gas, but preferably compressed air is used. A control switch, operating two three-way valves, control and direct the pressure and flow of the air to actuate the air cylinder. The valves can be located on the syringe filling apparatus itself or be remotely operated, using a foot pedal switch.

The three way valves direct pressurized air to enter through one of two entry/exit ports in the air cylinder, while gas is expelled from the other entry/exit port. The first port is located on the bottom side of the front of the air cylinder body, near the front bulkhead. A notch is cut into the spacer, to allow room for the first port. A second port is located on the bottom side of the air cylinder body, near the rear bulkhead. A slot is located on the bottom side of the slider, with the second port located between the sides of the slot, allowing the slider to move back and forth past the second port without restriction.

Pressurized gas that enters the first port will cause the rod to move outward from the body, causing the overall length of the air cylinder to increase. Expansion continues while sufficient pressure is applied, until the rod extends to its maximum length, or until a mechanical stop is encountered, preventing further expansion.

If the three way valve is actuated so that pressurized air is directed to the second port, the rod will slide into the body, causing the total length of the air cylinder to shorten or contract. During this contraction, any pressurized air in the front port area is expelled.

The slider and thumb plate gripper move with the rod. The syringe plunger thumb plate, positioned within the thumb plate groove, is moved along the same path as the thumb plate gripper, causing the plunger seal to move within the syringe barrel cavity.

When the air cylinder is expanding or shortening its length, the syringe barrel is held and gripped in position by the front and rear bulkheads, with the flanges positioned in the flange slot of the rear bulkhead. Since the barrel remains stationary, and the plunger is moving within the syringe barrel., the plunger seal's movement will increase or decrease the amount of volume within the syringe barrel cavity.

The plunger seal prevents any gas or material from entering or exiting through the rear end of the syringe barrel cavity. Since the overall cavity size is increased when the plunger seal moves towards the rear of the barrel cavity, a partial vacuum is created, causing the atmospheric pressure outside the syringe to act upon a liquid at the syringe's front port or needle opening, forcing it through the opening into the syringe barrel cavity.

When filling a syringe, the air cylinder length is expanded, until the plunger seal is moved to the desired position in the syringe cavity. Some liquids are extremely viscous, due to their physical nature and/or cold temperature. These liquids resist passing through a needle, or small opening, and can take some time to fully fill the barrel cavity. The pressurized gas within the air cylinder causes the plunger seal to maintain its position in the barrel cavity, creating a continuous vacuum during the filling process, without causing any strain upon the human worker. In some instances, the force on the plunger may be tailored, so that cavitation is avoided during the filling process. The force may be controlled directly by the level of pressure delivered to the air cylinder.

In some instances, small air bubbles may enter into the syringe during the filling process, being the result of residual air in the needle or port prior to filling, or due to cavitation. When syringes are filled manually, the technicians are required to remove any air bubbles that remain in the syringe barrel cavity after filling. Air bubbles have been traditionally removed by roughly thumping the side of the syringe barrel with a finger. If a person is engaged in the filling of numerous syringes, this type of manual thumping causes stress on the finger. Prolonged thumping can result in numbness and loss of sensitivity or feeling in the finger.

The syringe filling apparatus allows any air bubbles to be removed from syringes easily and efficiently, due to the hand held mobility of the device. Holding the syringe filling apparatus, so that the syringe port or needle is pointed upward, and tapping the bumper on a hard surface, dislodges air bubbles from the inner walls of the syringe barrel cavity and/or plunger seal. Once this occurs, the bubbles naturally move upward in the syringe barrel, lodging in the port. They are expelled by slightly pushing the plunger into the syringe barrel cavity. This can be done using force from the pressurized gas, or by simple manual operation.

Adjusting the gas pressure and flow rates, with regulators and flow control valves respectively, allows the operator to tailor the performance of the syringe filling apparatus to accommodate the varying viscosities of medications being drawn or dispensed. The delivered pressure to the air cylinder can be controlled through a regulator, or series of regulators that are either set or variable, to provide the desired force that will manipulate the syringe plunger. A variable flow control valve can be used to control the translation rate of the air cylinder and the syringe.

Typically, high pressure in a storage tank, or the pressure source, flows through a high pressure regulator, reducing the pressure to a steady lower level. In this system, a regulator would be set at 55 psi, and would feed into a draw line and a dispense line. The draw line delivers pressure to the first air entry/exit port, causing the air cylinder rod to move out of the body, lengthening the air cylinder, and pulling on the syringe plunger to fill the syringe with liquid. The dispense line delivers pressure to the second air entry/exit port, causing the air cylinder rod to move into the air cylinder body, dispensing the syringe contents.

Two separate air lines are used, so that different levels of pressure can be applied to the air entry/exit ports. Air cylinders require less air pressure to expand, than they do to contract, since the rod occupies some of the internal surface area in the air cylinder that the pressure acts upon. The 55 psi air is routed through two additional air line regulators so that the resultant pressure is 34 psi for the draw line, and 44 psi for the dispense line. This difference in pressure yields an equal fill and dispense force in the air cylinder. Using this level of pressure, with a ¾ inch air cylinder, a draw force, or vacuum of approximately 24 mm of mercury is reached within the syringe barrel.

Needle valve flow controls are placed in the draw and dispense lines, following the air line regulators, which allows the time delivery of the pressurized air to be adjusted for various liquid viscosities. Once the flow control is set for a specific liquid, syringes can be filled time and time again without cavitation.

A remote hand operated or foot controlled switch can be used to actuate valves that control the delivery of air pressure to the air cylinder itself. A hand actuated switch, located on the apparatus itself, provides the greatest amount of versatility and ease of use. The hand actuated valve assembly is fixed to the spacer, and has two bulkheads that each support a three way valve. A switch lever pivots between the bulkheads, and when moved from side to side actuates a valve rod in a three way valve. Each three way valve has an input air port, to receive pressurized air from a supply hose, fin output port, that directs air to the air cylinder, and an exhaust port, to vent the air cylinder to atmospheric pressure, when the hand actuated valve assembly is not being actuated. If venting was not possible, the pressure build up within the air cylinder would prevent the syringe from moving in either direction.

Venting the air cylinder to match atmospheric pressure makes it possible for the operator to remove unwanted air bubbles from the syringe. Manual manipulation of the syringe, while attached to the syringe filling unit, can be easily accomplished, since there is no residual pressure to contend with.

Once the air cylinder is vented, and the bubbles have moved to the nozzle of the syringe, the air cylinder rod can be manually urged into the cylinder body, gently dispensing the air bubbles out of the syringe.

The ability to move the syringe filler to various angles and locations, and the ability to turn the syringe to observe the graduation markings, allows this apparatus to be used at any angle to fill syringes from a variety of storage containers that may be impractical to move. The syringe filler, by virtue of its portability, allows the human operator to fill syringes that involve numerous dosages from a wide variety of liquids in a organized laboratory setting, without the need to move the source containers to the syringe.

In a medical setting, certain medicinal products are stored in small containers that require air to be inserted in them, prior to withdrawing fluid from them, so that a proper pressure is maintained following the withdrawal of the liquid. It is important to maintain the proper internal pressure within the syringe while disconnecting the syringe from a container. Any residual pressure within the syringe or container can cause unwanted spray of medication. Depending upon the liquid being used, the operator could be exposed to medical or physical hazards.

The syringe filling apparatus is designed to inject sufficient air into the container before drawing any contents out, and provide equal push and pull force on the syringe plunger. Both attributes contribute to the ability of the device to control proper pressure during the filling and dispensing process.

Certain liquids are stored in collapsible containers, that do not require air to be inserted into them, prior to having a portion of the liquid withdrawn. These containers can deliver the liquids to the syringe via a sterile tube, or by inserting the syringe needle directly into the container. The portable hand held use of the syringe filling apparatus allows the user to move to where the source container is, which is important in situations where ventilation hoods are required.

Connecting a dual check valve in the sterile tubing, between the source container and the syringe, allows the syringe filler to be used as a pumping or uniform delivery system. This allows fluid to be drawn into the syringe from the source container and then expelled out of the syringe through the double check valve into a receiving container.

An adjustable stop is used to limit the amount of fluid being drawn into the syringe. The stop is comprised of a shaft that is fixed at one end to the rear bulkhead, and extends toward the rear of the syringe filling apparatus, horizontal to the air cylinder rod. The shaft passes through a hole in the thumb plate gripper, allowing the slider and thumb plate gripper to move unobstructed, until the thumb plate gripper contacts a clamp that is positioned along the length of the shaft, with the clamp having a diameter that exceeds that of the hole in the thumb plate gripper. The length of the shaft may also be threaded, with a nut, or set of nuts, having a diameter that exceeds the hole in the thumb plate, used to provide the means for adjusting the stop.

Using the stop, the syringe filling device can be used as a pump to deliver exact quantities of liquid to a desired target container. If the stop is not used, the syringe filler can still operate as a pump, by delivering various amounts of liquids. Such use makes the need to have a freely rotatable syringe even more important, so that the technician can measure the liquid without error.

DESCRIPTION OF THE PREFERRED EMBODIMENT

Figures 1, 3:
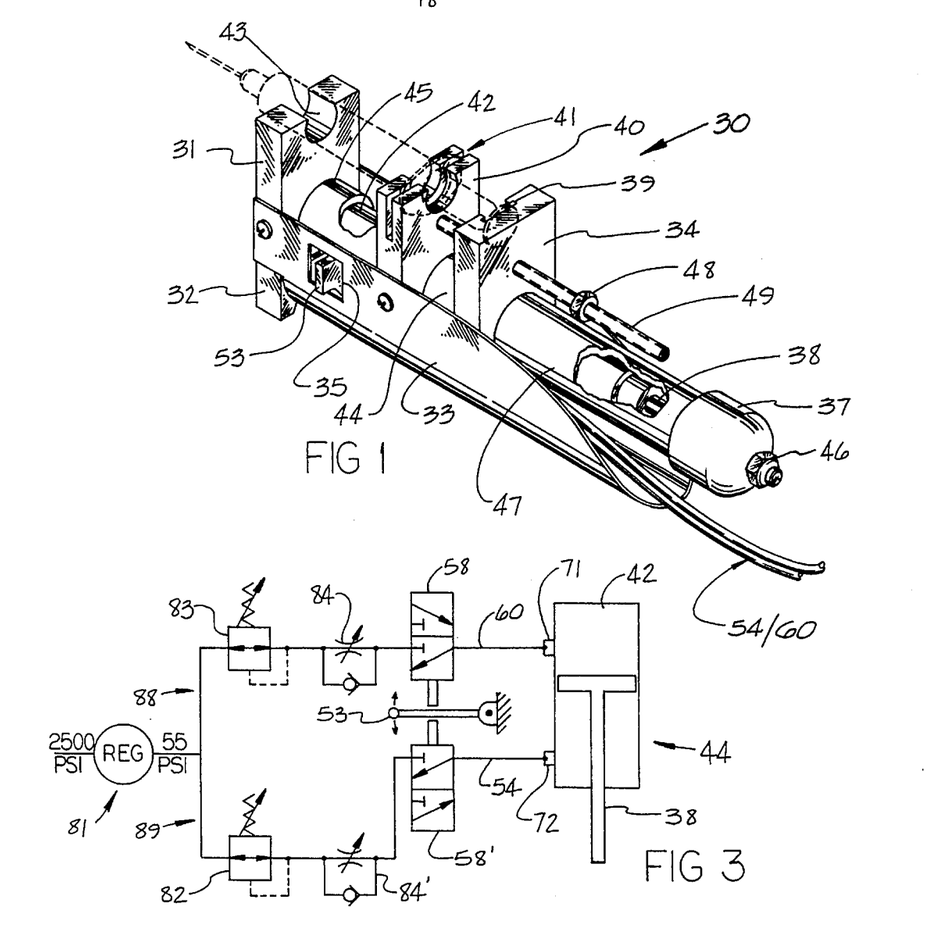
FIG. 1 is a perspective view from the top and side of the syringe filler.
FIG. 3 is a system functional diagram showing the various air pressure delivery lines, pressure modifiers and system components.

Referring to FIG. 1, a syringe 10, having a barrel 11, whose walls define the front and side walls of a cavity 14. A nozzle 12, at the front end of the syringe 10, defines an opening into the cavity 14. A hollow hypodermic needle 13 may be fixed to the nozzle 12. The barrel 11 has a set of flanges 16, which protrude outward from the length of the barrel 11.

A plunger 18 is slidably disposed within the barrel 11, with a thumb plate 17 on the rear end of the plunger 18, and a plunger seal 15 on the front end of the plunger 18. The plunger 18 moves horizontally within the barrel 11, with the plunger seal 15 contacting the walls defining the cavity 14, providing an airtight seal between the cavity 14 and the rear end of the barrel 11.

Referring also to FIG. 1, a syringe filler apparatus 30, having a front bulkhead 31 with supporting feet 32 on the bottom side, and a top side that defines a curved channel 43. This curved channel 43 follows a circular path that extends slightly over 180 degrees of circumference. A syringe barrel 11, when pushed into the curved channel 43, will snap into place, and be gripped by the side walls of the curved channel 43, so that the syringe barrel 11 cannot move vertically.

A double acting air cylinder 44 (air cylinder), has a front body 42, that is fixed to the front bulkhead 31, and a rod 38 with one end slidably disposed within the body 42, and the other end, being a threaded end, extending outward from the body 42 toward the rear of the syringe filling apparatus 30. The air cylinder rod 38 can slide horizontally forwards and backwards within the body 42. A protruding threaded end 90 (shown in FIG. 4), on the front of the body 42, passes through a rectangular hole in the front bulkhead 31, and is secured with a large retaining nut 51.

A rear bulkhead 40 is fixed to the rear end of the body 42, and has a top side that defines a curved channel with similar dimensions as the front bulkhead's curved channel 43. The top side of the rear bulkhead 40 also defines a flange slot 41. The flange slot 41 has a width, that can accommodate the width of a syringe flange 16, and a depth that allows the flange 16 to move freely within the flange slot 41 when the syringe barrel 11 is rotated. The front bulkhead 31 and rear bulkhead 40 are separated by a spacer 45, that encircles the air cylinder body 42.

A frame 33 is fixed to the front bulkhead 31 and the rear bulkhead 40, with the sides of the frame 33 forming a U-shaped channel that extends the length of the frame 33. The frame 33 and the air cylinder 44 are parallel to each other, with the air cylinder 44 positioned within the frame's 33 curved channel. The U-shaped channel of the frame 33 extends the length of the apparatus, and has a size and shape that allows a technician to hold and operate the syringe filling apparatus 30 using either the right or left hand.

A tube-shaped slider 47, having an end cap 37, is attached to the rod 38, using a nut or "bumper" 46, that tightens the end cap 37 to the rod's 38 threaded end. The slider 47 has a forward open end, with an internal diameter greater than the air cylinder's body portion 42. This allows the slider 47 to move forward over the front body portion 42, until it encounters the rear bulkhead 40, which acts as a stop, preventing further forward movement of the slider 47.

A thumb plate gripper 34 is fixed to the front of the slider 47, and extends out of the U-shaped channel of the frame 33. The top side of the thumb plate gripper 34 defines a groove 39, that can accommodate, the width of a syringe thumb plate 17. The groove 39 has a depth that allows the thumb plate 17 to rotate unhindered within the groove 39, when the syringe 10 is rotated.

Figures 2, 4:
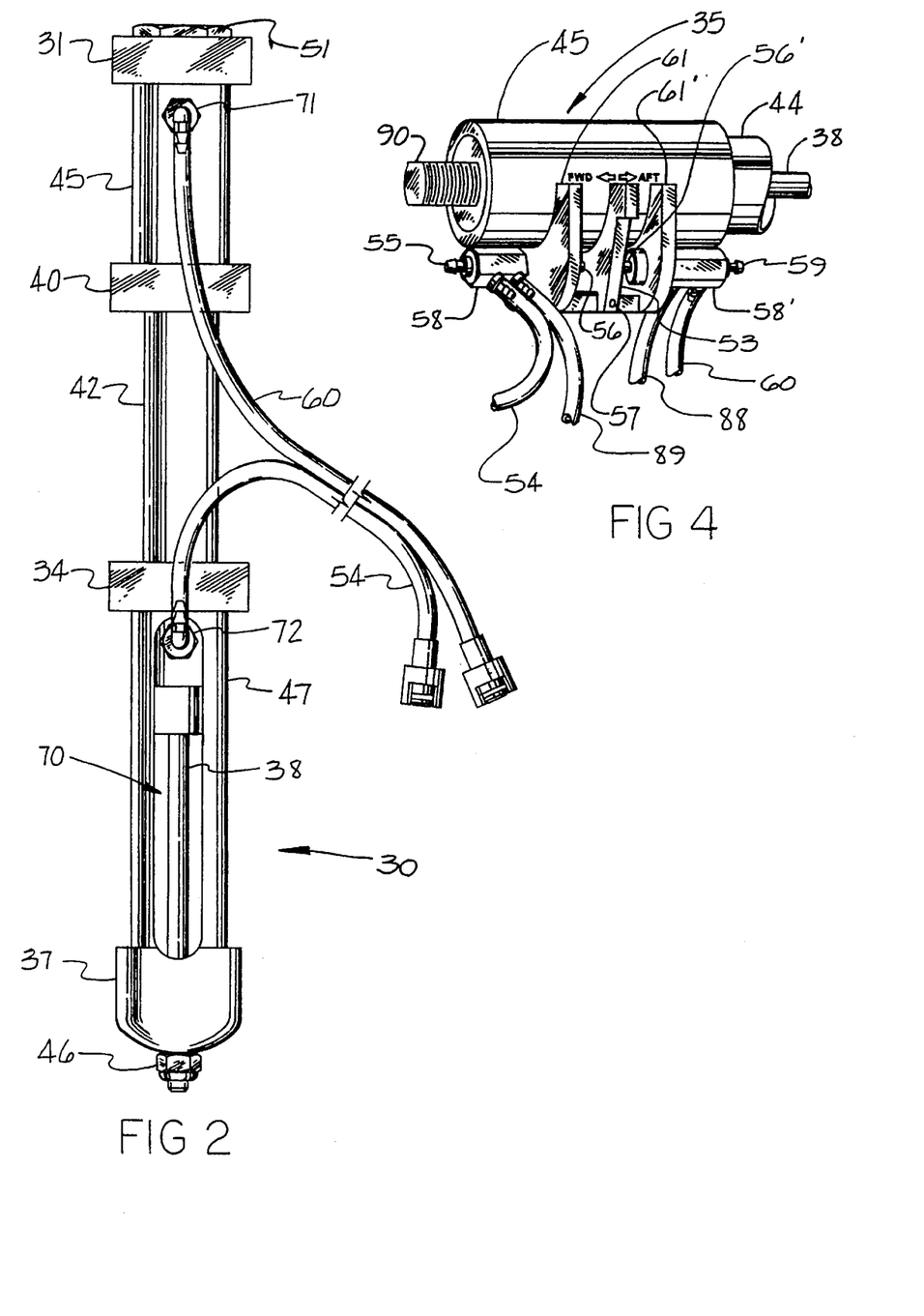
FIG. 2 is a perspective view of the bottom of the syringe filler apparatus.
FIG. 4 is a perspective view of the hand actuated valve assembly.

Referring to FIG. 2, the body 42 has a first air entry/exit port 71 ("first port"), and a second air entry/exit port 72 ("second port"). When pressurized gas is delivered through a drawing line 60 to the first port 71, the pressurized gas urges the rod 38 toward the rear of the body 42, causing the air cylinder's 44 total length to increase. When pressurized gas is delivered through a dispensing line 54 to the second port 72, the pressurized gas is urges the rod toward the front of the body 42, thereby shortening the overall length of the air cylinder 44.

The spacer 45 has a portion of it cut away to allow the first port 71 to protrude outward from the body 42. The slider 47 has a slot 70, which can accommodate the width of the second port 72, allowing the slider 47 to move horizontally. The second port 72 fits within the slot 70, and as the slider 47 moves along the length of the air cylinder 44, the side walls of the slot 70 engage the second port 72, maintaining the slider's 47 rotational alignment, keeping the thumb plate gripper 34 in a proper vertical position.

To place a syringe 10 on the syringe filling apparatus 30, the syringe barrel 11 is snapped into the front bulkhead curved channel 43, and a similar channel on the rear bulkhead 40. The syringe flanges 16 are positioned within the flange slot 41 of the rear bulkhead 40, and the thumb plate 17 is positioned within the groove 39 of the thumb plate gripper 34. The syringe plunger 18 can be horizontally manipulated, by sliding back and forth within the barrel 11, so that the thumb plate 17 can be properly positioned within the groove 39. The syringe 10 should be able to rotate, to allow optimal view of the graduated markings on the side of the syringe barrel 11.

Referring also to FIG. 4, the air cylinder 44 is actuated by a valve system switch, which can either be a remote foot controlled valve, or a hand actuated valve assembly 35, which can be attached to the syringe filling apparatus 30 itself, or a remote switch. Although both types of valve system switches will similarly direct pressurized gas to the syringe filling apparatus 30, a hand actuated valve assembly 35 provides the technician with a totally hand held portable system.

A hand actuated valve assembly (valve assembly) 35 is fixed to the spacer 45, with access to the actuating switch lever 53 available through both sides of the frame 33. The technician can manipulate the valve assembly with either the right or left hand using the fingers and palm of their hand to grip the frame, with their thumb manipulating the valve assembly 35.

The actuating switch lever 53 is situated between two bulkheads 61 and 61', and rotates around a pivot pin 57. The switch lever 53, when pivoted forward or aft,, depresses valve rod 56 or 56'. If valve rod 56 is depressed, it will actuate three way valve 58. If valve rod 56' is depressed, it will actuate three way valve 58'. The three way valves 58 and 58' are supported by the bulkheads 61 and 61', and control and direct the pressurized air to the first port 71 and second port 72 of the air cylinder 44.

The pressurized air is delivered to the hand actuated valve assembly 35, through draw line 88, which is connected to three way valve 58', and a dispense line 89, which is connected to three way valve 58. If a technician wishes to fill a syringe 10, they pivot the switch lever 53 in the direction they want the syringe plunger 18 to move. If the switch lever 53 is pivoted aft, or toward the rear of the syringe filling apparatus 30, the switch lever 53 depresses rod 56' into the three way valve 58', actuating it so that air entering through the draw line 88, is directed through the three way valve 58' to the output line 60, which is connected to the first port 71. The pressurized air urges the rod 38 out of the body 42, to extend the overall length of the air cylinder 44. The thumb plate gripper 34 pulls the syringe plunger 18 backwards, increasing the volume of the syringe cavity 14, drawing liquid into it. When the switch lever 53 is pivoted so that the valve rod 56' moves back to its original position, the directed air pressure ceases, and pressurized air from the first port 71 is vented through the exhaust 59.

If a technician wishes to push liquid out of a syringe 10, then the switch lever 53 is pivoted forward, depressing valve rod 56, actuating three way valve 58. The pressurized air in the dispense line 89, is directed through the output port 54 to the second port 72, which is located on the rear of the air cylinder body 42. The pressure urges the rod 38 to slide into the body 42, decreasing the overall length of the air cylinder 44. When the switch lever 53 pivots to its original position, the valve rod 56 also returns to its original position, allowing pressurized gas in the rear of the air cylinder body 42 to vent through an exhaust port 55.

As the rod portion 38 moves in and out of the body 42, the slider 47 and thumb plate gripper 34 are likewise moved. This movement causes the plunger seal 15 to slidably move within the syringe barrel 11. If the plunger seal 15 moves toward the front of the syringe 10, the available volume in the cavity 14 decreases. If there are any liquid substances within the cavity, it will be expelled through the nozzle 12 and/or needle 13 when the plunger seal 15 is pushed into the syringe barrel 11. If the plunger seal 15 is pulled toward the rear of the syringe 10, the volume of the cavity 14 will increase, creating a partial vacuum within the cavity 14, and substances under normal (greater) atmospheric pressure outside the syringe 10 will enter through the nozzle 12 and/or needle 13.

Liquid substances exhibiting high viscosity will enter into the syringe cavity 14 at a slower rate than substances exhibiting lower viscosity. In this situation, the pressure delivered to the air cylinder 44 can be tailored to a specific level, so that the necessary partial vacuum is created within the syringe cavity 14 during the filling procedure. Liquids with low viscosities will require less partial vacuum before they fill the syringe cavity 14. In this situation, the amount of gas pressure delivered to the air cylinder 44 should be reduced to avoid cavitation.

Referring also to FIG. 3, a pressure schematic diagram is depicted, showing the path of the pressurized gas, and the location of pressure modifiers along the path, prior to delivery of the pressurized gas to the air cylinder body 42. Pressurized gas can be obtained from a high pressure source, which is reduced through a regulator 81 to approximately fifty-five pounds per square inch ("psi"). The pressurized gas is directed to a draw line 88, and a dispense line 89.

The pressure in lines 88 and 89 are further reduced, with a draw line regulator 83 reducing the pressure to thirty four (34) psi, and the dispense line regulator 82 reducing the pressure to forty four (44) psi. Higher pressure levels are maintained in the dispense line 89, than the draw line 88, since the air cylinder rod 38 occupies some of the available surface area that the pressurized gas will act upon inside the air cylinder body 42, thereby reducing the force that the pressurized gas will have on the rod 38 within the body 42. Delivering forty four (44) psi to the second port 72 will provide a dispense force to the air cylinder 44 and syringe 10, equal to the draw force on the air cylinder 44 and syringe 10, when thirty four (34) psi is delivered to the first port 71.

Needle valve flow controls 84 and 84', with an unrestricted return, can modify the rate of delivery of pressurized gas along lines 88 and 89, to tailor the rate of the rod's 38 movement, so that the effects of cavitation are reduced during the filling process. The technician can pivot the switch lever 53 as necessary to actuate the three way valves 58 and 58', to deliver air in manually measured amounts to first port 71 and second port 72, allowing more accurate filling of the syringe cavity 14, and reducing the likelihood of cavitation.

If any unwanted air bubbles enter the cavity 14, they can be removed by positioning the syringe 10, while it is held in the syringe filler apparatus 30 to a vertical position, with the nozzle 12 and/or needle 13 pointed upward. This matter is simplified, since the syringe filler apparatus 30 can be held in a person's hand. To purge air bubbles, the bumper 46 on the cap 37, of the rear end of the slider 47 is gently tapped on a hard surface. The resulting vibrations are sufficient to dislodge air bubbles from the walls of the cavity 14. Once dislodged, the bubbles will move upward to the area of the nozzle 12, where they can be discharged from the syringe 10 by pushing the plunger seal 15 into the syringe barrel 11, either manually, or using pressurized air, which discharges a portion of the volume in the syringe cavity 14 including any air bubbles.

The syringe filling apparatus 30 can be used to either fill individual syringes or to be used as a pumping syringe for delivery of specific metered amounts to other syringes or containers, from a source container. To use the syringe filling device 30 as a pumping syringe, the syringe nozzle 12 is attached to a dual check valve that is fed by a bulk source container line. The air cylinder 44, when actuated, will expand and contract, so that the syringe 10 alternately draws and dispenses liquids, so that the syringe 10 operates as a pumping mechanism. A dual check valve directs the liquid to either enter the syringe during the drawing cycle, or be delivered to a target container when the syringe 10 dispenses.

The syringe filling apparatus 30 can use a syringe 10 to repeatedly dispense metered amounts of liquid. An adjustable stop is used to restrict the expansion movement of the rod 38 beyond a set point during the draw or fill cycle, so that the syringe 10 will receive a specific and metered amount of fluid during each fill cycle. The stop comprises a shaft 49, that is fixed to the rear bulkhead 40, and extends parallel to the double acting air cylinder rod 38, towards the end cap 37 and bumper 46. The length of the shaft 49 extends through a hole in the thumb plate gripper 34, allowing the thumb plate gripper 34 to move freely along the length of the rod 38, toward the rear of the syringe filling apparatus 30, until it encounters an object that is fixed to the shaft 49, having a diameter greater than the hole in the thumb plate gripper 34, which prevents any further rear movement of the thumb plate gripper 34.

The shaft 49 can have a smooth surface, using a clamping means, that can be firmly fixed to the shaft 49, and moved along the length of the shaft 49 to adjust the allowable rear movement of the thumb plate gripper 34. The shaft 49 can also have one or more notches along its length, to assist any clamping means with maintaining its grip and position on the shaft 49. Preferably, the shaft 49 will be threaded along its length, extending through one or more nuts 48, that are rotated, or moved and then snapped onto the threaded shaft 49 at their desired placement along the shaft 49.

When the syringe filler apparatus 30 is actuated to fill a syringe 10, the rod 38 moves the slider 47 and thumb plate gripper 34 backwards, until the thumb plate gripper 34 contacts the stop means, which is preferably a nut 48, preventing any further backward movement. When the syringe filling apparatus 30 is actuated to empty a syringe 10, the thumb plate gripper 34 moves forward with the slider 47 until forward progress is halted when the rod 38 has moved into the body 42 as far as possible, so that the slider 47 or thumb gripper 34 contacts the rear bulkhead 40, prohibiting any further forward movement.

The fluid to be measured out is dispensed from a large source container, with tubing attached to a dual check valve tee connector, which is connected to the syringe 10. The dual check valve allows fluid to enter the syringe cavity 14 during the filling cycle, and when the syringe 10 dispenses the fluid, the dual check valve directs the fluid into a discharge tube, to a target container or syringe. Each filling cycle, the thumb plate gripper 34 draws the syringe plunger 18 back in the syringe 10 until the thumb plate gripper 34 encounters the nut 48 on the threaded rod 49. At this point in time, the volume of the syringe cavity 14 has increased to its maximum volume, and fluid is allowed to enter the syringe 10. Once the syringe cavity 14 is completely filled, pressurized gas is then directed to the second port 72, causing the thumb plate gripper 34 to push the plunger 18 forward in the syringe 10, dispensing the fluid. The dispensed fluid is directed by the dual check valve into a dispense line, which is connected to a target container or target syringe.

By repeating these steps, the syringe filler apparatus 30 will fill and dispense an exact amount of liquid. The syringe filling apparatus 30, when used as a pumping mechanism, can be hand held, or placed on a flat surface.

From the foregoing statements, summary and description in accordance with the present invention, it is understood that the same are not limited thereto, but are susceptible to various changes and modifications as known to those skilled in the art and we therefore do not wish to be limited to the details shown and described herein, but intend to cover all such changes and modifications which would be encompassed by the scope of the appended claims.

I claim:

1. A portable syringe filling apparatus for drawing and dispensing controlled or variable amounts of liquid, comprising:
   (a) a double acting cylinder, having a body, and a rod slidably disposed within the body;
   (b) a front bulkhead, fixed to the front of the body of the double acting cylinder, having a curved channel for gripping the barrel portion of a hypodermic syringe;
   (c) a rear bulkhead, fixed to the rear end of the body of the double acting cylinder, having a curved channel for gripping the barrel portion of a hypodermic syringe, with a flange slot;
   (d) a slider, attached to the double acting cylinder rod end, having a sufficient internal diameter that allows the slider to move over the body of the double acting cylinder;
   (e) a thumb plate gripper, fixed to the slider, and having a groove for receiving a syringe thumb plate;
   (f) a valve assembly, having an actuating switch lever, so that when moved it is able to actuate one of two three way valves;
   (g) a draw line, connected to a three way valve in the valve assembly and to a first port on the double acting cylinder body;
   (h) a dispense line, connected to a three way valve in the valve assembly and to a second port on the double acting cylinder body.

2. A portable syringe filling apparatus for drawing and dispensing controlled or variable amounts of liquid, as recited in claim 1, in which the curved channel, defined by the front bulkhead and rear bulkhead follows a circular path that extends slightly over 180 degrees of circumference, so that when a syringe barrel is pushed into the curved channel, it will snap into place and be gripped by the side walls of the curved channel.

3. A portable syringe filling apparatus for drawing and dispensing controlled or variable amounts of liquid, as recited in claim 1, in which the front bulkhead and rear bulkhead are fixed to a frame that forms a U-shaped channel, with the U-shaped channel having a size and shape that allows a technician to hold and operate the portable syringe filling apparatus.

4. A portable syringe filling apparatus for drawing and dispensing controlled or variable amounts of liquid, as recited in claim 1, in which the rear bulkhead acts as a stop on forward movement of the slider, which prevents movement of the slider over the body of the double acting cylinder past the rear bulkhead.

5. A portable syringe filling apparatus for drawing and dispensing controlled or variable amounts of liquid, as recited in claim 1, in which a syringe barrel is held by the front and rear bulkhead's curved channels, and where the syringe is able to rotate freely within the curved channel and flange slot, to allow optimal view of the graduated markings on the side of a syringe barrel.

6. A portable syringe filling apparatus for drawing and dispensing controlled or variable amounts of liquid, as recited in claim 1, in which the valve assembly actuating switch lever has three positions:
   (a) an aft position which actuates a three way valve so that pressure is directed to the draw line, through the first port on the double acting cylinder body, in which the pressure pushes the rod outward from the double acting cylinder body;
   (b) a forward position, which actuates a three way valve in the dispense line, directing pressure to a second port, located on the rear of the double acting cylinder body, so that the rod is urged into the double acting cylinder body;
   (c) an original position, in which neither three way valve is actuated, and all pressurized gas in the double acting cylinder is vented.

7. A portable syringe filling apparatus for drawing and dispensing controlled or variable amounts of liquid, as recited in claim 1, in which a draw line regulator sets the pressure in the draw line lower than the pressure in the dispense line.

8. A portable syringe filling apparatus for drawing and dispensing controlled or variable amounts of liquid, as recited in claim 1, in which a dispense line regulator sets the pressure in the dispense line higher than the pressure in the draw line.

9. A portable syringe filling apparatus for drawing and dispensing controlled or variable amounts of liquid, as recited in claim 1, in which the valve assembly has an actuating lever foot pedal, which can direct pressurized air to the first port, second port, or to neither port so that any pressure in the double acting cylinder is vented.

10. A portable syringe filling apparatus for drawing and dispensing controlled or variable amounts of liquid, as recited in claim 1, in which a second port is located on the rear of the body of the double acting cylinder, and where the slider defines a slot having side walls that engage the second port as the slider moves, maintaining the slider's rotational alignment to keep the thumb plate gripper in a proper vertical position.

11. A portable syringe filling apparatus for drawing and dispensing controlled or variable amounts of liquid, as recited in claim 1, in which actuating valve assembly is positioned on a spacer, that fits around the body of the double acting cylinder, in between the front and rear bulkhead.

12. A portable syringe filling apparatus for drawing and dispensing controlled or variable anoints of liquid, as recited in claim 1, in which an adjustable stop is used to restrict the movement of the slider and rod beyond a set point during the draw cycle, so that a syringe will receive a specific and metered amount of fluid, where the adjustable stop comprises a shaft that is fixed to the rear bulkhead and extends parallel to the double acting cylinder rod, extending through a hold in the thumb plate gripper, with an object, that can be fixed to the shaft, in which the object has a diameter greater than the hole in the thumb plate gripper.

13. A method of drawing and dispensing controlled or variable amounts of liquid, to avoid cavitation, comprising the steps of:
   (a) fitting a syringe, that is fitted to a source liquid, onto a syringe filling apparatus, by pushing the syringe barrel into the curved channels of the front and rear bulkheads, and positioning the thumb plate into the thumb plate gripper on an apparatus comprising a double acting cylinder, having a body, and a rod slidably disposed within the body; a front bulkhead, fixed to the front of the body of the double acting cylinder, having a curved channel for gripping the barrel portion of a hypodermic syringe; a rear bulkhead, fixed to the rear end of the body of the double acting cylinder, having a curved channel for gripping the barrel portion of a hypodermic syringe, with a flange slot; a slider, attached to the double acting cylinder rod end, having a sufficient internal diameter that allows the slider to move over the body of the double acting cylinder; a thumb plate gripper, fixed to the slider, and having a groove for receiving a syringe thumb plate gripper; a valve assembly, having an actuating switch lever, so that when moved it is able to actuate one of two three way valves; a draw line, connected to a three way valve in the valve assembly and to a first port on the double acting cylinder body; a dispense line, connected to a three way valve in the valve assembly and to a second port on the double acting cylinder body;

(b) setting pressure in the draw line so that it is lower than the pressure in the dispense line;

(c) moving the actuating switch lever from an original position to an aft position, so that pressure from the draw line urges the double acting cylinder rod outward from the body, which moves the syringe plunger backwards, so that fluid can move into the syringe barrel;

(d) allowing desired amount of fluid to enter the syringe;

(e) moving the actuating switch lever back to the original position, and allowing pressure in the double acting cylinder to vent;

(f) moving the actuating switch lever to a forward position, so that pressure from the dispense line urges the double acting cylinder rod back into the body, pushing the plunger forward in the syringe barrel to dispense fluid;

(g) moving the actuating switch lever back to the original position, once the desired amount of fluid has been dispensed, causing all pressure in the double acting cylinder to vent.

\* \* \* \* \*